(12) United States Patent
Ansell

(10) Patent No.: US 7,829,551 B2
(45) Date of Patent: Nov. 9, 2010

(54) METHOD AND COMPOSITION FOR THE CONTROL OF ARTHROPODS

(75) Inventor: Jayne Ansell, West Sussex (GB)

(73) Assignee: Durminster Limited, Road Town, Tortola (VG)

( * ) Notice: Subject to any disclaimer, the term of this patent is extended or adjusted under 35 U.S.C. 154(b) by 906 days.

(21) Appl. No.: 11/705,389

(22) Filed: Feb. 12, 2007

(65) Prior Publication Data

US 2007/0142330 A1     Jun. 21, 2007

Related U.S. Application Data

(60) Division of application No. 10/097,615, filed on Mar. 15, 2002, now abandoned, which is a continuation of application No. PCT/GB00/03540, filed on Sep. 14, 2000.

(30) Foreign Application Priority Data

| Sep. 16, 1999 | (GB) | 9921858.8 |
| Jan. 17, 2000 | (GB) | 0000947.2 |
| Feb. 24, 2000 | (GB) | 0004445.3 |
| Aug. 4, 2000 | (GB) | 0019099.1 |
| Aug. 10, 2000 | (GB) | 0019758.2 |

(51) Int. Cl.
   *A61K 31/695*   (2006.01)
   *A01N 25/34*   (2006.01)

(52) U.S. Cl. .................................. 514/63; 424/405

(58) Field of Classification Search ................... 514/63; 424/405
See application file for complete search history.

(56) References Cited

U.S. PATENT DOCUMENTS

| 4,146,619 A | 3/1979 | Lover et al. |
| 4,654,328 A | 3/1987 | Itoh et al. |
| 4,656,162 A | 4/1987 | Itoh et al. |
| 5,045,536 A | 9/1991 | Baker |
| 5,288,483 A | 2/1994 | Cardin et al. |
| 5,609,878 A | 3/1997 | Gueyne et al. |
| 6,274,130 B1 | 8/2001 | Murray |

FOREIGN PATENT DOCUMENTS

| EP | 0 191 543 | 8/1986 |
| GB | 2246708 A | 2/1992 |
| GB | 2 275 419 | 8/1994 |
| WO | 92/09264 A2 | 6/1992 |
| WO | WO 98/01032 | 1/1998 |
| WO | 99/41986 A1 | 8/1999 |
| WO | WO 01/13954 | 3/2001 |

OTHER PUBLICATIONS

International Cosmetic Ingredient Dictionary and Handbook, *CTFA, Seventh edition*: 431-432 and 437-438 (1997).

*Primary Examiner*—Shengjun Wang
(74) *Attorney, Agent, or Firm*—Edgar W. Harlan; Carolyn S. Elmore; Elmore Patent Law Group PC

(57) ABSTRACT

The present invention relates to the use of certain siloxanes and mixtures thereof in the control of arthropods such as insects and arachnids, and in particular ectoparasites, such as head lice.

7 Claims, No Drawings

METHOD AND COMPOSITION FOR THE CONTROL OF ARTHROPODS

RELATED APPLICATIONS

This application is a divisional of U.S. application Ser. No. 10/097,615, filed Mar. 15, 2002, now abandoned which is a continuation of International Application No. PCT/GB00/03540, Sep. 14, 2002, which designated the United States and was filed on Sep. 14, 2000, published in English, which claims priority under 35 U.S.C. §119 or 365 to Great Britain (GB) Application No. 9921858.8, filed Sep. 16, 1999, GB Application No. 0000947.2, filed Jan. 17, 2000, GB Application No. 0004445.3, filed Feb. 24, 2000, GB Application No. 0019099.1, filed Aug. 4, 2000 and GB Application No. 0019758.2, filed on Aug. 10, 2000. The entire teachings of the above applications are incorporated herein by reference.

This invention relates to the use of organo-silicon derivatives in controlling and repelling arthropods such as insects and arachnids, and to novel organo-silicon containing formulations. In particular the invention relates to the use of siloxanes for the control and eradication of head lice and their ova.

Head lice frequently infest human hair and are easily spread by contact. Such infestations are particularly prevalent among children of school age and in the associated institutional environment can spread rapidly. The louse itself is mobile and the female of the species can lay many hundreds of eggs in its lifetime. A female louse can lay fertile eggs as soon as 12 days after hatching. Transfer of the mature lice leads to the spread of infestation while the adhesion of eggs to hair ensures a reservoir of lice in each infested head. The empty egg shells are commonly referred to as "nits".

Eradication of head lice involves total removal or destruction of both the mature lice and the eggs on each host. Various attempts have been proposed to achieve such destruction but none are wholly satisfactory.

The eggs and mature lice may be removed by combing the hair with a special comb having very fine gaps between the teeth. Such combing should remove all mature lice and destroy the bond between the eggs and the hair so that the combing action releases the eggs or catastrophically ruptures them. For the host subject regular combing with a "nit comb" is a painful and undignified procedure. It is known that hair conditioning will aid the management of head lice by coating the hair cuticle with conditioning agents that in turn allow easier grooming with a fine toothed comb. Some of these products use relatively small amounts of silicones together with a wide variety of other components. However the use of conditioners do not repel or effectively eliminate head lice. A recent study (*Lancet* 2000; 356:540) has demonstrated that combing methods are significantly less effective in eradicating head lice than the use of insecticidal shampoos.

In an alternative procedure the hair is treated with an insecticidal spray or washed with an insecticidal shampoo. One approved and widely used insecticide for this purpose is malathion, an organo-phosphorus compound. This compound has an unpleasant odour and causes allergic reactions in some subjects. Insecticides are not entirely effective so that reinfestation can occur. Organic insecticides such as hexachlorocyclohexane, malathion and pyrethrins can cause toxic responses in humans such as nerve damage. Such responses are considerably more dangerous than the head lice infestations which they are used to treat. Furthermore head lice can mutate and develop resistance to insecticides of this nature.

It has been proposed that vegetable oils, such as olive oil, should be used to treat head lice infestations by causing suffocation. Such treatment has the disadvantage that application of the oil is unpleasant both for the person applying the oil and the person to whom it is applied. Removal of the oil from treated hair requires the use of strong detergents which tend to damage the hair cuticle and destroy the hair's natural protection from head lice infestation.

UK Patent No. 1,604,853 (Stafford-Miller Limited) describes the use of linear alkyl or aryl siloxane polymers such as dimethicone, phenyldimethicone and simethicone having a viscosity of less than 20,000 centistokes for controlling ectoparasites in particular lice and/or their ova.

International Application WO98/01032 (Bayer AG) describes arthropod-repellent mixtures comprising:
(1) 1-15% by weight of an arthropod repelling active substance;
(2) 1-10% by weight of a silicone polymer;
(3) 50-98% by weight of one or a plurality of cyclic silicones; and
(4) optionally further auxiliary agents or solvents.

There is however no indication that the siloxanes themselves have any insecticidal effect.

Silicone polymers are widely used in personal care products in particular hair care products such as shampoo and conditioners. GB 2 246 708 A describes hair conditioning compositions comprising a blend of a volatile silicone component and a non-volatile silicone component. There is no suggestion in this application that silicone products have any insecticidal properties.

In view of concerns about the toxic effect of insecticidal shampoos, it is often preferred to use either the dry combing method or the wet-combing method, often with the aid of conditioners, particularly for the treatment of head lice in children.

There is thus clearly a requirement for a safe and effective method of eradicating head lice.

We have now surprisingly found that certain siloxane formulations are highly effective in eradicating both head lice and their ova.

Thus, in a first aspect the present invention provides the use of a composition comprising as active ingredient at least one siloxane derivative, other than solely a linear alkyl or aryl siloxane having a viscosity less than 20,000 centistokes, for the control of arthropods, in particular insects and arachnids e.g. ectoparasites and/or their ova.

The siloxane may for example be selected from:
(i) a linear siloxane, other than solely a linear alkyl or aryl siloxane having a viscosity less than 20,000 centistokes;
(ii) a branched siloxane;
(iii) a cyclic siloxane; and
(iv) a silicone copolymer.

The invention extends to mixtures of said siloxanes, as well as to mixtures of said siloxanes with linear alkyl or aryl siloxanes having a viscosity less than or equal to 20,000 centistokes.

It will be understood that viscosity can be expressed as absolute viscosity, which is measured in poises (gsec$^{-1}$cm$^{-1}$) or centipoises, or as kinematic viscosity. Kinematic viscosity is the ratio of viscosity to density and is measured in stokes or centistokes. For convenience herein viscosity will be expressed in centistokes unless otherwise stated. Where the density of a substance is close to 1, absolute and kinematic viscosity have almost the same numercial values.

In this specification, "controlling" arthropods such as insects and arachnids e.g. ectoparasites includes repelling, reducing in number and eradicating said arthropods e.g. ectoparasites. Control of ova includes killing and reducing the viability of said ova. Use of the compositions in controlling arthropods includes prophylactic use.

Preferably the invention provides the use of a composition comprising a non-volatile siloxane and a volatile siloxane for the control of arthropods such as insects and arachnids e.g. ectoparasites and their ova.

It will be appreciated that there is no absolute definition of the terms "volatile" and "non-volatile" but their meaning in the context of the present invention will be apparent to those skilled in the art.

For the purposes of this application the term "volatile" is taken to mean that the material has a measurable vapour pressure at 25° C., i.e. usually fluids with a viscosity of less than approximately 50 centistokes. The non-volatile siloxane will generally have a boiling point above approximately 300° C. or a viscosity above about 50 centistokes. Volatile siloxanes, which may be either linear or cyclic siloxanes, generally have a boiling point below 300° C. or a viscosity below 50 centistokes, preferably below 10 centistokes.

The siloxane derivative may be selected for example from one of the many siloxanes known for use in personal care products such as shampoos and conditioners. Such compounds are described for example in GB 2155788 A, EP A 433946, GB 2144329 A, EP A 333433 and GB 2246708 A. For the avoidance of doubt, the term "siloxane" as used herein is intended to encompass silicones.

Siloxanes which may be employed in the present invention include, but are not limited to, linear or branched polysiloxanes of the general formula (I):

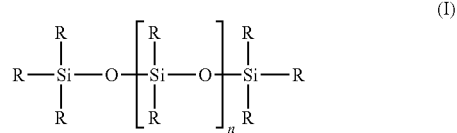

(I)

where n is from 1 to about 15,000, preferably from 20-7000. Substituents R can be independently chosen from one or more of linear, branched or cyclic alkyl groups containing 1 to 20, e.g. 1-16 carbon atoms, aryl substituents such as phenyl, naphthyl, substituted phenyl, or substituted naphthyl, a siloxane chain so as to give a branched silicone, hydrogen, or vinyl groups. In addition, substituents R may also contain further functional groups attached to carbon such as one or more of alkenyl, alkynyl, carboxyl, hydroxy, acrylate, ester, ether, alkoxy, halogen, cyano, mercapto, amino and carbohydrate groupings. The substituents contained in R may be neutral or contain cationic centres such as quaternary ammonium or anionic centres such as sulphonic acid or thiosulfate groupings. Additionally the siloxane may contain terminal OH groups, i.e. siliconol materials. The R group in commercially available siloxanes is predominantly methyl.

This variety of silicones is exemplified by, but not limited to the following general formula (II)-(V) where R and n are both as defined above and m is chosen such that m+n may equal up to about 15000:

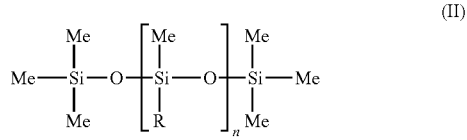

(II)

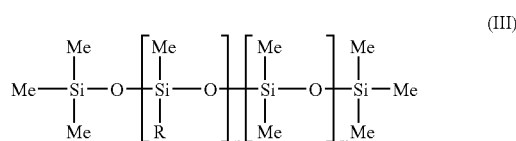

(III)

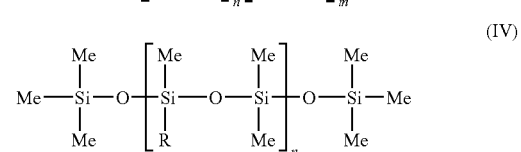

(IV)

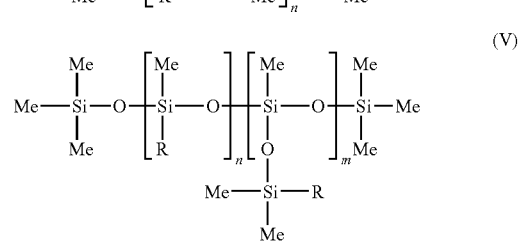

(V)

It will be appreciated that the viscosity and hence volatility of the siloxanes of formula (I)-(V) will depend on the specific values of n, m and R. In the siloxanes (I) values of n from 1 to about 4 will generally give volatile compounds, while compounds wherein n is >4 will generally be regarded as non-volatile.

It will also be appreciated that a linear alkyl or aryl siloxane having a viscosity of less than 20,000 centistokes will only be employed in admixture with one or more other siloxane derivatives as defined above.

Examples of linear siloxanes include hexamethyldisiloxane, octamethyltrisiloxane, decamethyltetrasiloxane, low viscosity trimethylendblocked polydimethylsiloxanes, phenyl trimethicone and dimethicones. Commercially available products include those available as Dow Corning 200, 556, 2502 and 5324 (all Trade Marks of Dow Corning).

Preferred functional siloxanes for use in the present invention include compounds of formula (I) wherein at least one R group is OH. A particularly preferred compound of this type is dimethiconol.

Cyclic siloxanes which may be employed in the present invention include, but are not limited to, those of general formula (VI)

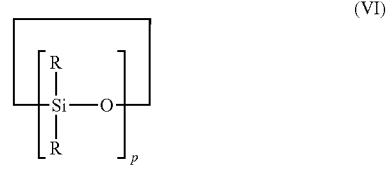

(VI)

wherein R is as defined above and p is from 3 to 10. The viscosity and hence volatility will depend upon the values of R and p. For a non-volatile cyclic siloxane where R is $CH_3$, n should be greater than 7, preferably greater than 8. For all values of n it is preferred that R is not H or OH, or that only a small percentage of the R groups have these values.

Cyclic siloxanes are preferably volatile siloxanes of the formula (VII):

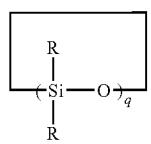

(VII)

where each R is independently selected from an alkyl group consisting of 1 to 10 carbon atoms, an aryl group consisting of 6 to 10 carbon atoms, hydrogen and vinyl; and q has the value of 3 to 7. The preferred cyclic silicones for use in the present invention are those where R predominantly comprises the group —$CH_3$ and q is 4, 5 or 6 of a mixture thereof.

Examples of volatile cyclic siloxanes which may be employed include decamethylcyclopentasiloxane, octamethylcyclotetrasiloxane and hexamethylcyclotrisiloxane, or mixtures thereof. Preferred cyclic siloxanes for use in the present invention are cyclomethicones which are blends of poly-dimethylcyclosiloxanes available as e.g. Dow Corning 245 (™) (cyclopentasiloxane) and Dow Corning 345 (™) (a mixture of cyclopentasiloxane and cyclohexasiloxane).

Siloxane copolymers for use in the present invention may include those containing glycol or other ether functions which may be exemplified by, but are not limited to those of general formula (VIII):

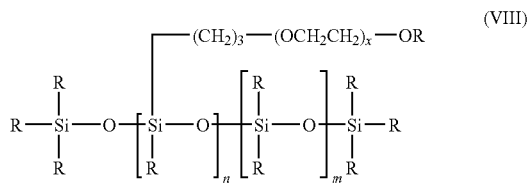

(VIII)

wherein n, m and R are as defined above and x is chosen, depending on n and m, so as to give a copolymer with a molecular weight typically in the range of 1000-30,000 and a non-siloxane content of between 25 and 90%. Such compounds typically have viscosities in the range 40-4000 centistokes.

Examples of such silicones include dimethicone copolyol, commercially available as Dow Corning 193 (™).

It will be appreciated by those skilled in the art that commercially available siloxane products may be obtained in a range of viscosity grades. For example, Dow Corning 200 (™) is available at viscosities of from 0.65 to 60,000 centistokes. It will further be understood that the appropriate viscosity grade should be selected, depending upon whether a volatile or non-volatile siloxane is required. It will also be understood that the percentage by volume of the volatile siloxane may vary depending upon the amount of the non-volatile siloxane in the composition.

It will be appreciated that the viscosity of non-volatile siloxanes may vary widely from around 50 centistokes up to over 100,000 centistokes. It will therefore be understood that the proportion of non-volatile siloxane in the composition will at least in part depend upon its viscosity. For example a non-volatile siloxane in the lower range of viscosity e.g. from 50-350 centistokes may comprise more than 50% e.g. up to 99% of the composition.

Compositions for use according to the present invention preferably comprise from 50-99.9% by volume of a volatile siloxane, more preferably from 85-99.9% by volume, e.g. 90 to 99% by volume of a volatile siloxane and from 0.1-50% by volume of a non-volatile siloxane, more preferably 0.1 to 15% e.g. 1 to 10% by volume of a non-volatile siloxane.

Most preferably the volatile siloxane comprises 97.5 to 95.5% and the non-volatile siloxane comprises 2.5 to 4.5% of the formulation.

The non-volatile siloxane is preferably a linear siloxane derivative, in particular a dimethicone or most preferably a dimethiconol.

The volatile siloxane is preferably a cyclic siloxane such as cyclopentasiloxane or cyclomethicone.

A composition for use according to the invention preferably consists essentially of siloxanes, and may consist of 1.00% siloxanes.

If desired, however, the basic siloxane composition may include one or more additives which may include analgesics, antiseptics, anti-inflammatories and repellents. Such additives form a minor proportion of the composition, usually less than 1%, but in certain cases may be present up to 3%.

Additives may be essential oils, in particular those which have analgesic, antiseptic, anti-inflammatory and/or repellent properties. Such oils include feverfew, cedarwood, clove, geranium, lavender, lemon, rosemary, cinnamon, juniper, lemon grass, myrrh, neroli, peppermint, opine, rose, sage, sandalwood or tea tree oils. Camomile essence may also be added as an analgesic.

The additives used in the composition may be subject to change through the effects of sunlight, heat and other storage conditions. To reduce such changes known preservative compounds, such as anti-oxidants and ultra-violet radiation absorbing compounds may be included.

Further compounds e.g. surfactants may be added to the fluid composition of the invention so that it has detergent properties and may act as a shampoo while at the same time retaining its insecticidal properties. Such compositions perform the dual functions of cleaning hair and both removing any head lice and nits present and providing residual protection against reinfestation.

The siloxane composition may also be incorporated into other formulations suitable for use on the hair, e.g. as a mousse, gel, lotion, spray and the like.

Formulations for use according to the present invention may be prepared in conventional manner. Such formulations preferably comprise at least 50%, more preferably 75% and advantageously at least 85% of the siloxane composition.

The viscosity of the finished composition including any additives or excipients may conveniently be in the range 1 to 350 centistokes, preferably 3 to 100 centistokes and advantageously 15 to 35 centistokes.

As indicated hereinbefore, compositions for use according to the invention are useful in the control of arthropods, particularly terrestrial arthropods, especially insects and arachnids. Insects include ectoparasites. In particular said compositions have pediculicidal and ovicidal activity, and are therefore especially useful for treating infestations of lice in animals, including humans.

Ectoparasites include sucking and biting lice, fleas, keds, mites and ticks. Sucking lice (Anoplura) and biting lice (Mallophaga) are parasites found on nearly all groups of mammals, and include *Haematopinus* spp., *Linognathus* spp., *Solenopotes* spp., *Pediculus* spp., and *Pthirus* spp. *Pediculus* spp. include *Pediculus humanus*, e.g. the head louse *pediculus*

*humanus capitis* and the body or clothing louse *pediculus humanus humanus*. *Pthirus* spp. includes the crab louse *Pthirus pubis*.

Head lice possess a hard chitinous exoskeleton which serves as protection from external elements. Lice eggs (ova) are similarly protected by a chitinous sheath surrounding the egg. Although lice may be affected by use of an insecticide, the eggs often remain resistant to attack. Without wishing to be bound by theory it is believed that in respect of lice the siloxane compositions act by causing rupture and dehydration of the lice. It is also believed that the compositions may affect the lipid coat of the lice. It is further believed that the volatile siloxane component enhances the effect of the non-volatile component.

It is believed that the compositions will also be useful for the control of other terrestrial arthropods, including for example public health pests e.g. cockroaches and bed bugs; nuisance arthropods e.g. wasps, ants, silver fish and woodlice; and structural pests e.g. furniture beetles, deathwatch beetles and other wood borers.

In a second aspect the present invention provides the use of a siloxane derivative selected from:
(i) a linear siloxane, other than solely a linear alkyl or aryl siloxane having a viscosity less than 20,000 centistokes;
(ii) a branched siloxane;
(iii) a cyclic siloxane; and
(iv) a silicone copolymer;

in the manufacture of a medicament for controlling arthropods such as insects and arachnids and/or their ova, in animals including humans.

In a third aspect the present invention provides a method of controlling arthropods, such as insects and arachnids, which comprises applying to said arthropod a siloxane derivative selected from:
(i) a linear siloxane, other than solely a linear alkyl or aryl siloxane having a viscosity less than 20,000 centistokes;
(ii) a branched siloxane;
(iii) a cyclic siloxane; and
(iv) a silicone copolymer.

Preferred features of the second and third aspects are as for the first aspect of the invention.

For use in treating head lice and/or their ova the siloxane composition may be applied to the hair and scalp of a subject infested with head lice. The action of the siloxane components kills or incapacitates the lice, and the ova. For a single treatment the siloxane composition is preferably used in an amount of from 25 to 50 ml depending upon hair length and thickness. It will. be understood that these dosage levels relate to the composition in undiluted form, i.e. containing at least 95% siloxanes. If the composition is used in diluted form e.g. as a shampoo, the actual volume employed should be increased accordingly to maintain an effective level of the active component(s).

Following application e.g. to the head and scalp, the siloxane composition preferably remains in contact with the affected area for a period of from 10 minutes to 12 hours. Lice may generally be destroyed within a period of 5-20 minutes. A longer period may be required to kill the ova, and it is preferred that the composition remains in contact with the ova for a period of 8-12 hours, for example overnight. It should be understood that the composition may if desired be left on the hair for a longer period without adverse effect on the host subject.

Following treatment with the siloxane composition the hair may be washed with a mild shampoo, to remove the dead lice and ova. The non-volatile siloxane component of the composition leaves a coating of siloxanes on the hair. This acts as a lubricant, allowing any remaining ova to be combed out of the hair and preventing any subsequently laid eggs forming an adhesive bond with the hair. The residue therefore also has a prophylactic effect. If necessary the treatment may be repeated to destroy any lice emerging after the first application remaining ova. Such second application is preferably 7-12 days after the first treatment.

The siloxane compositions may also find veterinary application, for example for the control of parasites on non-human animals. The animal is preferably a mammal or a bird and may include for example, cattle, pigs, sheep, goats, horses, deer, fowl e.g. hens, as well as companion animals, such as dogs and cats.

For use in the control or eradication of other insects the siloxane composition may be formulated in any appropriate manner.

In a fourth aspect the present invention provides a novel siloxane composition comprising a cyclomethicone, preferably cyclopentasiloxane or cyclohexasiloxane or a mixture thereof, in admixture with dimethiconol, wherien the cyclomethicone comprises 96.5-97.5 by volume and the dimethiconol comprises 2.5-3.5% by volume.

The invention will now be further illustrated by the following non-limiting examples:

Methods

Adult female and male lice, *Pediculus humanus*, in approximately equal numbers, were counted into batches and provided with squares of an open meshed nylon gauze (tulle) as a substrate upon which to stand during the test. Louse eggs were obtained by providing actively reproductive adults with a close meshed nylon gauze as an egg laying substrate over a 48 hour period.

The silicone mixtures were used either undiluted or mixed 1:3 by volume with tap water to simulate application of the material to wetted hair. Mixtures of silicone fluids were made on a weight for weight (w/w) basis. The negative Control employed was tap water.

For the test procedure, the lice or eggs were first immersed in the liquid for 10 seconds. After removal from the fluid they were blotted to remove any excess liquid and incubated under normal maintenance conditions (30°±2° Celsius and 60%±15% relative humidity). At the end of the exposure period the insects and gauze were rinsed three times using 250 milliliters of warm (34° Celsius) tap water poured through and over the gauze squares. They were then blotted dry using medical wipe tissue and incubated until the results were recorded. In the case of lice this was after 24 hours and for eggs after all the Control batch had completed hatching, approximately 12 days.

Results

TABLE 1

Activity of D5D* preparations on human lice

| Treatment | Number of replicates | Number of lice Total | Killed | Moribund | Mortality % |
|---|---|---|---|---|---|
| D5D undiluted 20 minutes | 15 | 303 | 300 | 3 | 100 |
| D5D 1:3 in water 20 minutes | 1 | 20 | 20 | 0 | 100 |
| Control | 1 | 182 | 9 | 2 | 6.0 |

*D5D is cyclopentasiloxane containing 3.3% dimethiconol w/w

TABLE 2

Activity of D5D* preparations on human louse eggs

| Treatment & application | Replicate | Number of eggs | | | | Mortality %** | Undeveloped %** |
|---|---|---|---|---|---|---|---|
| | | Total | Hatched | Half-hatched | Undeveloped | | |
| D5D undiluted Overnight | 1 | 63 | 10 | 2 | 37 | | |
| | 2 | 132 | 38 | 3 | 66 | | |
| | 3 | 202 | 23 | 4 | 130 | | |
| | Total | 397 | 71 | 9 | 233 | 82.1 (75.9) | 58.7 (49.3) |
| D5D 1:3 in water 20 minutes | 1 | 199 | 132 | 5 | 51 | | |
| | 2 | 189 | 130 | 6 | 38 | | |
| | 3 | 90 | 62 | 3 | 22 | | |
| | Total | 478 | 324 | 14 | 111 | 32.2 (8.8) | 23.2 (5.8) |
| Control | 1 | 106 | 78 | 1 | 20 | | |
| | 2 | 149 | 116 | 1 | 19 | | |
| | 3 | 216 | 156 | 2 | 48 | | |
| | Total | 471 | 350 | 4 | 87 | 25.7 | 18.5 |

*D5D is cyclopentasiloxane containing 3.3% dimethiconol w/w
**Mortality and the proportion of eggs failing to show eye spots (Undeveloped) are recorded as the gross mortality followed in parentheses by the figure adjusted for Control mortality, using Abbot's correction. The corrected mortality is the true figure by which the activity of the treatment should be measured.

TABLE 3

Activity on human lice of volatile silicone solvents

| Treatment | Number of Replicates | Number of lice | | | |
|---|---|---|---|---|---|
| | | Total | Killed | Moribund | Mortality % |
| DC 193$^a$ (™) 20 minutes | 1 | 20 | 20 | 0 | 100 |
| DC 345$^b$ (™) 20 minutes | 3 | 60 | 44 | 14 | 96.7 |
| Control | 2 | 40 | 3 | 1 | 10.0 |

$^a$DC 193 (™) = dimethicone copolyol
$^b$DC 345 (™) = cyclomethicone

TABLE 4

Activity on human lice of dimethiconol dissolved in volatile silicone solvents

| Treatment | Replicate | Number of lice | | | |
|---|---|---|---|---|---|
| | | Total | Killed | Moribund | Mortality % |
| 345 (™)$^b$ + dimethiconol 20 minutes | 1 | 19 | 19 | 0 | 100 |
| 556 (™)$^c$ + dimethiconol 20 minutes | 1 | 21 | 21 | 0 | 100 |
| Control | 1 | 20 | 2 | 1 | 15.0 |

$^b$DC 345 (™) = cyclomethicone
$^c$DC 566 (™) = phenyl trimethicone

TABLE 5

Activity on human lice of high molecular weight dimethicones

| Treatment | Replicate | Number of lice | | | Mortality % |
|---|---|---|---|---|---|
| | | Total | Killed | Moribund | Total (Killed) |
| Dimethicone 30K CS 3.3% | 1 | 20 | 14 | 5 | 95 (70) |
| Dimethiconol 100K CS 3.3% | 1 | 22 | 21 | 0 | 95.5 (95.5) |
| Control | 1 | 20 | 2 | 0 | 10 (10) |

The invention claimed is:

1. A method for controlling lice on a human subject, which comprises contacting the lice with a siloxane composition consisting essentially of a non-volatile siloxane having a viscosity of 100,000 centistokes and a volatile siloxane, wherein the siloxane composition consists essentially of 97.5% to 95.5% by volume of the volatile silicone and 2.5 to 4.5% by volume of the non-volatile silicone.

2. The method according to claim 1, wherein the non-volatile siloxane is a linear siloxane and the volatile siloxane is a cyclic siloxane.

3. The method according to claim 1, wherein the non-volatile siloxane is a dimethicone.

4. The method according to claim 1, wherein the non-volatile siloxane is a dimethiconol.

5. The method according to claim 1, wherein the volatile siloxane is a cyclomethicone.

6. The method according to claim 5, wherein the cyclomethicone is a cyclopentasiloxane or a mixture of cyclopentasiloxane and cyclohexasiloxane.

7. The method according to claim 1, wherein the lice are *Pediculus humanus*.

* * * * *